United States Patent [19]

Shim

[11] 3,943,198

[45] *Mar. 9, 1976

[54] POLYALKYLENE GYLCOL VINYL PHOSPHATES

[75] Inventor: Kyung S. Shim, Irvington, N.Y.

[73] Assignee: Stauffer Chemical Company, Westport, Conn.

[ * ] Notice: The portion of the term of this patent subsequent to June 25, 1991, has been disclaimed.

[22] Filed: July 22, 1974

[21] Appl. No.: 490,595

Related U.S. Application Data

[63] Continuation-in-part of Ser. No. 410,674, Nov. 12, 1973, which is a continuation-in-part of Ser. No. 86,313, Nov. 2, 1970, Pat. No. 3,819,756, which is a continuation-in-part of Ser. No. 63,262, Aug. 6, 1970, abandoned.

[52] U.S. Cl. ...... 260/929; 260/2.5 AJ; 260/2.5 AR; 260/45.7 P; 260/DIG. 24
[51] Int. Cl.² ........................................... C07F 9/11
[58] Field of Search .................................... 260/929

[56] References Cited
UNITED STATES PATENTS

| | | | |
|---|---|---|---|
| 3,819,750 | 6/1974 | Shim | 260/929 |
| 3,878,270 | 4/1975 | Shim | 260/929 X |

*Primary Examiner*—Anton H. Sutto
*Attorney, Agent, or Firm*—Richard P. Fennelly

[57] ABSTRACT

Polyalkylene glycol vinyl phosphates having the formula:

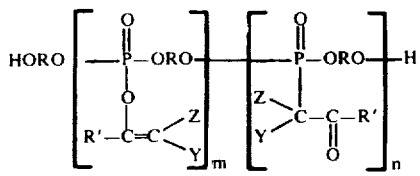

are provided wherein R is a polyalkylene glycol residue, $m$ and $n$ are integers from about 1 to about 100, R' is selected from the group consisting of hydrogen, lower alkyl, and lower haloalkyl, provided that if R' is lower haloalkyl, it is not monohalo-substituted on its alpha carbon atom, and Z and Y are selected from the group consisting of hydrogen, lower alkyl and lower haloalkyl. They are formed by reacting the transesterification product of a tertiary phosphite and a polyalkylene glycol with a carbonyl compound having halogen monosubstitution on one of its alpha carbon atoms. These compositions can be used to flame retard a number of normally flamable substrates.

4 Claims, No Drawings

POLYALKYLENE GYLCOL VINYL PHOSPHATES

RELATED APPLICATION

This application is a continuation-in-part of Application Ser. No. 410,674, filed Nov. 12, 1973, which, in turn, is a continuation-in-part of U.S. application Ser. No. 86,313, filed Nov. 2, 1970, now U.S. Pat. No. 3,819,756, which in turn was a continuation-in-part of U.S. application Ser. No. 63,262, filed Aug. 6, 1970, now abandoned.

BACKGROUND OF THE INVENTION

In the polyurethane field, increased interest is being shown in compounds which can be added to the polyurethane polymers to act as fire retardant agents. Particular interest is being shown in compounds which have functional groups reactive with the polyol or polyisocyanate used in preparing the polyurethane so that the fire retardant agent can be copolymerized into the polymer chain. One such group of compounds of this type are the polyalkylene glycol polyphosphites and phosphonates. In general, these materials are prepared by transesterifying a secondary phosphite with a polyalkylene glycol in the presence of an alkaline catalyst such as sodium phenolate or sodium methylate. However, many of these materials have relatively high acidity causing them to react with and thereby deactivate certain catalyst systems generally used in the formation of polyurethane polymers such, for example, as tertiary amine compounds. To alleviate this problem, the polyalkylene glycol phosphonates have heretofore been reacted with materials such as alkylene oxides in order to reduce the number of acid groups on the phosphorus. However, addition of the alkylene groups onto the phosphorus has decreased the relative flame retardancy of these compounds. Alternatively, secondary polyalkylene glycol phosphites have been reacted with carbon tetrachloride or chloral in order to add flame retardant chlorine atoms to the molecule. However, the phosphonates formed in this manner are still relatively high in acidity.

Therefore, it is an object of the present invention to produce a class of compounds which are compatible with polyurethane foams, which can be copolymerized therewith, which have a high degree of flame retardancy and which are relatively low in acidity. Various other objects and advantages of this invention will be apparent from a reading of the disclosure which follows hereinafter.

TECHNICAL DESCRIPTION OF THE INVENTION

It has now been discovered that this object can be realized by employing novel polyalkylene glycol phosphites, produced by transesterifying a tertiary phosphite with a polyalkylene glycol, and reacting the polyphosphite so obtained with a carbonyl compound which has monohalogen substitution on its alpha carbon atom. The composition so formed has both vinyl and carbonyl side chains due to Perkow and Arbuzov rearrangement reactions. The novel compounds of the present invention have a formula corresponding to:

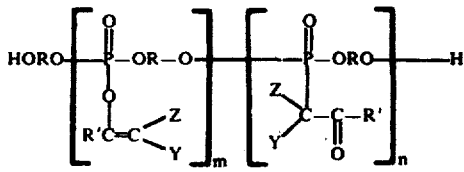

wherein m and n are each numbers having a value of from 1 to about 100, Y and Z are each selected from the group consisting of hydrogen, lower alkyl, i.e., $C_1$-$C_4$ alkyl groups, and haloalkyl groups, R is a polyalkylene glycol residue and R' is hydrogen, lower alkyl having from 1 to 4 carbon atoms or lower haloalkyl, provided that if R' is lower haloalkyl it is not monohalosubstituted on its alpha carbon atom. It can be di-halo or tri-halo substituted. The product has the m and n moieties either randomly or regularly distributed through the polymer chain.

The term "polyalkylene glycol residue" is meant to designate that portion remaining after two hydroxyl groups have been removed from a polyalkylene glycol having the formula:

wherein R'' is an alkylene group of from 2 to about 20 carbon atoms, and m' designates the number of repeating alkylene ether units and is normally from 2 to about 20.

A tertiary phosphite is initially reacted with a polyalkylene glycol to yield the intermediate polyalkylene glycol phosphite. The term "tertiary phosphite" as used herein is meant to designate compounds having the formula:

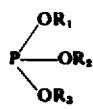

wherein $R_1$, $R_2$ and $R_3$ are each alkyl having from 1 to about 10 carbon atoms or aryl. Illustrative of the alkyl groups are methyl, ethyl, propyl, butyl, hexyl and the like. The term alkyl is also intended to include substituted alkyl groups, including aromatic substituted alkyls such as benzyl substituted groups and the like. Illustrative of the aryl groups are phenyl and naphthyl groups and substituted forms thereof. The tertiary phosphites which are preferred for use in the present invention are trimethyl phosphite, the most preferred compound, triethyl phosphite, tributyl phosphite, triphenyl phosphite, dimethyl ethyl phosphite, and methyl diethyl phosphite.

The selected tertiary phosphite is transesterified with a polyalkylene glycol. The term "polyalkylene glycol" as used herein is meant to designate those compounds having a formula corresponding to:

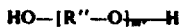

wherein R'' and m' are as defined above. Illustrative of the polyalkylene glycols which can be employed in the present invention are: diethylene glycol, triethylene glycol, dipropylene glycol, the most preferred compound, tripropylene glycol, dibutylene glycol, tributylene glycol, polyethylene glycols where the average number of ether units is 2, polypropylene glycols where the average number of ether units is 14, trihexylene glycol and the like.

The transesterification step is accomplished by reacting the tertiary phosphite with the polyalkylene glycol in approximately a 1:1 molar ratio. By employing this equimolar proportion of reactants, polyalkylene phosphites having the formula:

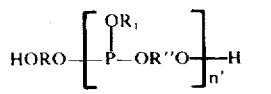

wherein $R_1$ and $R''$ are as above and $n'$ is from 1 to 100, are obtained. The temperature at which the transesterification step is conducted is from about 80°C. to about 200°C. and preferably at from about 100°C. to about 150°C.

This reaction can be improved by employing any of the well known transesterification catalysts. Particularly useful catalysts are the alkali metal alcoholates and phenolates such as sodium methylate, sodium phenolate, sodium decylate and the like. These catalysts are normally employed in an amount from 0.01 to 5 percent, by weight of the entire reactant mixture. The degree of transesterification can be measured by the quantity of by-product alcohol formed. For example, when 1 mole of trimethyl phosphite is reacted with 1 mole of tripropylene glycol, the transesterification is completed when 2 moles of methanol has been evolved. The reaction time will vary over a wide range depending upon the reactants, temperature and catalyst used. Normally reaction times will be in the range from about 0.5 to 50 hours.

The polyalkylene phosphite produced by the transesterification step is then reacted with a carbonyl compound having mono-substitution on its alpha carbon atom and having the formula:

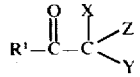

where $R'$, $Z$ and $Y$ are as defined above and $X$ is bromine or chlorine. These carbonyl compounds can be illustrated by the following: monochloroacetone, monobromoacetone, chloroacetaldehyde, bromoacetaldehyde, chloromethyl ethyl ketone, bromomethyl ethyl ketone and the like. Particularly preferred compounds for use in the present invention are monochloroacetone and monobromoacetone.

The carbonyl compounds defined above are normally reacted with the transesterification product in approximately equimolar proportions with respect to the starting tertiary phosphite. The reaction is conducted at a temperature in the range from about 0° to about 100°C., and, preferably, at from about 10°C. to about 40°C. The reaction can be monitored by determining the amount of alkyl or aryl chloride byproduct formed. The reaction is complete when approximately 1 mole of chloride has been formed for each mole of carbonyl compound employed.

Both the transesterification and the subsequent reaction with the carbonyl compound can, if desired, be carried out in the presence of a solvent or diluent although this is not necessary to the invention. The solvent or diluent should be non-reactive with respect to both the starting materials and the desired products, and should be miscible therewith. The solvent can also form an azeotrope with the by-product alkanol or phenol of the transesterification step. Illustrative of suitable solvents are benzene xylene, ethylbenzene, diethylbenzene, various alkanes having boiling points greater than that of the by-product, and the like.

The novel compounds of the present invention are characterized by their ability to copolymerize with polyisocyanates employed in forming polyurethanes and by their relatively low acidity. These compounds can completely replace the polyols normally employed in forming the foams or they may be used in combination with the polyols, thereby yielding foams with greatly improved flame resistance. The acid numbers of the compounds of the present invention are normally below about 2 mg. of KOH per gram of the polyalkylene glycol vinyl phosphates. This low acidity makes these compounds relatively unreactive toward the polymerization catalysts employed in producing the polyurethane foams. The high percentage of the flame retardant phosphorus and chlorine atoms present in these compounds reduces the concentration necessary to achieve a flame resistant foam.

A further advantage of the compounds of the present invention is their ability to render the foam self-extinguishing. This characteristic is particularly important in the area of flexible urethane foams. Normally the compounds of the present invention can be employed in amounts of from about 5 to about 30 percent, by weight of foam to yield self-extinguishing flexible foams. The amount will vary depending upon the particular foam used.

The novel compounds of the present invention can also be used as flame retardants in a wide variety of polymeric systems as is desired in greater detail in my U.S. Pat. No. 3,819,750 and my copending U.S. application Ser. No. 410,674 which are each incorporated herein by reference. Illustrative of these systems are: polyurethane foams, the preferred embodiment, polyesters, polyolefins, cellulose ethers and esters, urethane coatings and many others. These compounds can also be employed in combination with any of the known flame retardants, whether reactive or non-reactive, and can also be used as the sole flame retardant in foams or polymers.

The present invention will be further illustrated by the following Examples. Unless otherwise stated, all parts and percentages are by weight.

EXAMPLE I

In a 500 ml flask was placed 134 g. (1 mole) of dipropylene glycol, 124 grams (1 mole) of trimethyl phosphite and 0.3 g of sodium methoxide, and these reactants were heated to 104°C. with rapid stirring. After about 4 hours methanol had stopped distilling out of the flask. The heating was continued at 100°C. under an aspirator pressure of 25mm Hg for 2 hours. At this time the mixture was cooled to room temperature and 150 ml of benzene was added. This solution was vigorously stirred and 1 mole of monochloroacetone (92.5g) was added at room temperature. The temperature rose to 34°C. for an hour, and it was thereafter allowed to cool to room temperature. The solution was stirred overnight.

The next day the mixture was heated to 70°–80°C. at an aspirator pressure of about 20 mm Hg to remove solvent and other volatiles. The product was 229 g of an oil having a neutral acid number of OH numbers of 38 (isocyanate demand method) and 101 (acetic anhydride method). Subsequent analysis confirmed that the compound had a structure as defined in formula I above.

EXAMPLE II

To a 500 ml funnel with stirrer, thermometer, dropping funnel and reflux condenser were added 194g (1 mole) of the compound of formula II described above. Benzene (74.4g) was also added and the mixture was cooled in ice water. At 10°C. the addition of monochloroacetone (brown color) was begun. No exothermic reaction occurred. The mixture was then stirred, and it was heated slowly to 100°C. At about 40°C. condensation was observed on the sides of the flask. Some of the benzene was removed as the temperature rose above about 80°C. The temperature was maintained at about 100°C. for 3 hours. At the end of this time the solvent was stripped. The residual oil was dark brown, had a weight of 220g and an acid No. of 1.47. The hydroxy numbers in two separate analyses were 108 and 132. The % P in these two were 10.6% and 10.7% (the theoretical being 13.13%). Subsequent analyses showed the product to have the structure shown in Formula I, above.

EXAMPLE III

The product from Example I was incorporated into a polyurethane foam. The following Table sets forth the reagents which were added in formulating this foam:

| Reagent | Amount (in grams) |
|---|---|
| Product from Ex. I | 30 |
| Polyol | 200 |
| Silicone Surfactant | 1.8 |
| Water | 8.0 |
| N-ethyl morpholine | 0.4 |
| Niax A-1 (amine catalyst) | 0.35 |
| CH$_2$Cl$_2$ | 6.0 |
| Stannous Octoate (50% in dioctyl phthalate) | 0.8 |
| Toluene diisocyanate (80%-2,4 isomer, 20% 2,6-isomer) | 105.8 |

The rise time was 125 seconds, and a postcure at 120°C. for 1 hour was performed. The foam had an average density of 1.63 lbs/ft and an average air flow of 4.39 ft/min.

Samples of the foam was evaluated by ASTM-1692 for flame retardancy, and it self-extinguished in an average of 53 seconds after 2.8 inches of foam had burned. The average burn rate was 1.42 min/sec.

What is claimed:

1. Polyalkylene glycol vinyl phosphates having the formula:

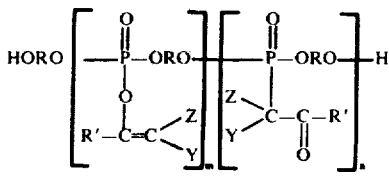

where R is a polyalkylene glycol residue formed by removing two hydroxyl groups from a polyalkylene glycol having the formula:

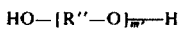

where R'' is an alkylene group of from 2 to 20 carbon atoms and $m'$ is an integer from 2 to 20, $m$ and $n$ are each integers of from about 1 to 100, R' is selected from the group consisting of hydrogen, lower alkyl and lower haloalkyl, provided that when R' is lower haloalkyl, monohalo substitution is absent on its alpha carbon atom, and Z and Y are each selected from the group consisting of hydrogen, lower alkyl and lower haloalkyl.

2. A composition as claimed in claim 1 wherein R is a dipropylene glycol residue.

3. A composition as claimed in claim 1 wherein R' is a methyl group.

4. A composition as claimed in claim 1 wherein Z and Y are both hydrogen.

* * * * *